(12) United States Patent
Knappe et al.

(10) Patent No.: US 10,327,999 B2
(45) Date of Patent: Jun. 25, 2019

(54) BLOWING AGENT-CONTAINING HAIR CARE COSMETIC

(71) Applicant: Henkel AG & Co. KGaA, Duesseldorf (DE)

(72) Inventors: Thorsten Knappe, Schenefeld (DE); Ulrike Heinsohn, Hamburg (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/186,217

(22) Filed: Jun. 17, 2016

(65) Prior Publication Data

US 2016/0287490 A1 Oct. 6, 2016

Related U.S. Application Data

(63) Continuation of application No. PCT/EP2014/074303, filed on Nov. 12, 2014.

(30) Foreign Application Priority Data

Dec. 20, 2013 (DE) .................. 10 2013 226 807

(51) Int. Cl.
  *A61K 8/04* (2006.01)
  *A61Q 5/06* (2006.01)
  *A61K 8/39* (2006.01)

(52) U.S. Cl.
  CPC ............... *A61K 8/046* (2013.01); *A61K 8/39* (2013.01); *A61Q 5/06* (2013.01)

(58) Field of Classification Search
  CPC ............. A61K 8/39; A61K 8/046; A61Q 5/06
  See application file for complete search history.

(56) References Cited

U.S. PATENT DOCUMENTS

| 2008/0305064 A1 | 12/2008 | Bui et al. |
| 2010/0021396 A1* | 1/2010 | Kleen ............ A61K 8/046 424/47 |
| 2011/0268684 A1 | 11/2011 | Battermann et al. |
| 2014/0341817 A1 | 11/2014 | Mueller et al. |

FOREIGN PATENT DOCUMENTS

| WO | 2010130626 A2 | 11/2010 |
| WO | 2015081935 A1 | 6/2015 |
| WO | 2015081937 A1 | 6/2015 |

OTHER PUBLICATIONS

PCT International Search Report (PCT/EP2014/074303) dated Jan. 13, 2015.
Gao et al., "A New Multifunctional, Shine-enhancing Emollient: PPG-3 Benzyl Ether Mysristate", XP009077503, Journal of Cosmetic Science, vol. 55 (Supplement), pp. S143-S150, 2004.

\* cited by examiner

*Primary Examiner* — Sreenivasan Padmanabhan
*Assistant Examiner* — Genevieve S Alley
(74) *Attorney, Agent, or Firm* — P. Scott Smith

(57) ABSTRACT

Aerosol compositions, comprising a) at least one propellant and b) at least one cosmetic preparation, including (i) at least one strengthening active substance and (ii) at least one alkoxylated carboxylic acid ester of the following formula (I), in which R1 represents a straight-chain or branched, saturated or unsaturated alkyl group having 6 to 24 carbon atoms, R2 represents hydrogen or an alkyl group having 1 to 4 carbon atoms, R3 and R4 represent, independently of each other, hydrogen or an alkyl group having 1 to 4 carbon atoms, R5 represents a straight-chain or branched, saturated or unsaturated alkyl group having 6 to 24 carbon atoms or a phenyl group, and n and m represent, independently of each other, the numbers 0 or 1 to 20, are suitable for the application of hair cosmetic agents in the form of spray mists, quickly collapsing foams.

4 Claims, No Drawings

BLOWING AGENT-CONTAINING HAIR CARE COSMETIC

FIELD OF THE INVENTION

The present invention generally relates to the technical field of temporarily shaping keratin-containing fibers, particularly human hair. Aerosol compositions, including at least one propellant and a cosmetic composition, which includes at least one strengthening active substance and at least one specific hair care substance, and the use of these compositions to temporarily shape keratin-containing fibers are the subject matter of the present invention.

BACKGROUND OF THE INVENTION

Keratin-containing fibers are understood to include, in principle, all animal hair, e.g., wool, horsehair, angora hair, furs, feathers, and products or textiles produced therefrom. However, the keratin fibers are preferably human hair.

An attractive hairstyle is generally considered to be an indispensable part of a well-groomed appearance today. Because of current fashion trends, hairstyles which, for many hair types, can be created and/or maintained for a long time period to several days only by using strengthening active substances are again and again considered desirable. Therefore, hair treatment agents that are used to permanently or temporarily shape the hair play an important role. While the chemical structure of the keratin-containing fiber is modified by reduction and oxidation in the case of permanent shaping, such modifications of the chemical structure do not occur in the case of temporary shaping. Corresponding agents for temporary shaping typically include synthetic polymers and/or waxes as the strengthening active substance. Agents for supporting the temporary shaping of keratin-containing fibers can be prepared as hair spray, hair wax, hair gel, and hair mousse, for example. In particular, application in the form of a spray or a foam by means of aerosol dispensing containers is very popular.

The most important property of an agent for temporarily shaping keratin fibers, also referred to as a styling agent below, consists in giving the treated fibers the strongest possible hold in the newly formed shape, i.e., the shape applied to the fibers. If the keratin fibers are human hair, this is also referred to as strong hairstyle hold or a high degree of hold of the styling agent. The hairstyle hold is determined mainly by the type and amount of the strengthening active substances used, wherein the further constituents of the styling agent and the form of application can also have an influence.

In addition to a high degree of hold, styling agents should also meet a range of further requirements. These can be roughly divided into properties on the hair, properties of the particular formulation, e.g., properties of the foam or of the sprayed aerosol, and properties relating to the handling of the styling agent, wherein the properties on the hair are especially important. In addition to moisture resistance and/or low tackiness, a balanced care effect is particularly noteworthy. Furthermore, a styling agent should be universally usable for all hair types to the extent possible and should be gentle on the hair and skin.

In order to meet the different requirements, a large number of synthetic polymers that are used in styling agents have been developed as strengthening active substances in the prior art. The polymers can be divided into cationic, anionic, non-ionic, and amphoteric strengthening polymers. When the polymers are applied to the hair, the polymers ideally result in a polymer film, which on the one hand gives the hairstyle strong hold but on the other hand is sufficiently flexible not to be break under load. If the polymer film is brittle, film flakes are formed, i.e., residues that detach when the hair is moved and give the impression that the user of the corresponding styling agent has dandruff. Similar problems result if waxes are used as a strengthening active substance in the styling agent.

Application in the form of an aerosol in particular requires additional measures. It should be possible to distribute the aerosol product well on the keratin-containing fiber, i.e., it should be possible to apply the composition evenly as a fine spray mist in a targeted manner in the case of products in the form of an aerosol spray. If the composition is applied in the form of an aerosol foam, this foam should be voluminous and stable enough to be applied to the fibers. At the same time, however, this foam should collapse easily on the fiber to ensure that the fibers are adequately wetted with the composition.

An especially important requirement that a modern styling agent should also meet is an adequate care effect. In particular, a care effect is taken to mean that, after the application of the styling agents, the hair has a soft texture and shine, is easy to comb, and has high volume and high flexibility. In the past, however, the incorporation of common hair care active substances into styling agents sometimes led to worse hold of the hair.

Therefore, the problem addressed by the present invention was that of providing agents for temporarily shaping keratin-containing fibers that are distinguished by a high degree of hold and that can be applied well to the keratin-containing fibers. It should be possible to apply the agents to the fiber particularly as a fine, targeted spray mist or as a quickly collapsing foam. Furthermore, the agents should leave behind on the hair an optimal balance between satisfying hold and conditioned hair feel.

The combination of a propellant with a cosmetic composition, which includes a specific hair care active substance in addition to a strengthening active substance, is suitable for solving this problem.

Furthermore, other desirable features and characteristics of the present invention will become apparent from the subsequent detailed description of the invention and the appended claims, taken in conjunction with this background of the invention.

BRIEF SUMMARY OF THE INVENTION

An aerosol composition, comprising at least one propellant and at least one cosmetic preparation, including at least one strengthening active substance and at least one alkoxylated carboxylic acid ester of the following formula (1),

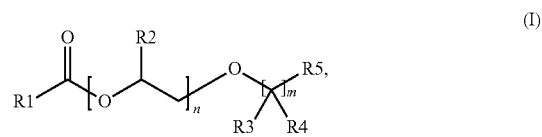

in which R1 represents a straight-chain or branched, saturated or unsaturated alkyl group having 6 to 24 carbon atoms; R2 represents hydrogen or an alkyl group having 1 to 4 carbon atoms; R3 and R4 represent, independently of each other, hydrogen or an alkyl group having 1 to 4 carbon atoms; R5 represents a straight-chain or branched, saturated or unsaturated alkyl group having 6 to 24 carbon atoms or a phenyl group; and n and m represent, independently of each other, the numbers 0 or 1 to 20.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The present invention relates first to an aerosol composition, including
a) at least one propellant and
b) at least one cosmetic preparation, which includes
 (i) at least one strengthening active substance and
 (ii) at least one alkoxylated carboxylic acid ester of the following formula (I),

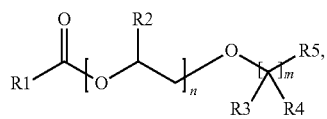
(I)

in which
R1 represents a straight-chain or branched, saturated or unsaturated alkyl group having 6 to 24 carbon atoms,
R2 represents hydrogen or an alkyl group having 1 to 4 carbon atoms,
R3 and R4 represent, independently of each other, hydrogen or an alkyl group having 1 to 4 carbon atoms,
R5 represents a straight-chain or branched, saturated or unsaturated alkyl group having 6 to 24 carbon atoms or a phenyl group, and
n and m represent, independently of each other, the numbers 0 or 1 to 20.

The aerosol compositions according to the invention comprise a) a propellant, b) a cosmetic preparation, and optionally further active substances and/or auxiliary substances.

A first essential constituent of the aerosol compositions according to the invention is the strengthening active substance included in the cosmetic preparation. In the temporary shaping of keratin-containing fibers, a strengthening active substance within the meaning of the invention contributes to the hold of the applied shape of the fibers (particularly the hold of a hairstyle or of the hair volume in the case of hair). The curl retention test is often used as a test method for the strengthening effect of an active substance.

Preferred aerosol compositions according to the invention are characterized in that the percentage of the strengthening active substance (i) by weight with respect to the total weight of the aerosol composition is 0.5 to 12 wt. %, preferably 1.0 to 10 wt. %, and particularly 2.0 to 8.0 wt. %.

Strengthening polymers or waxes, for example, are suitable as strengthening active substances.

In one embodiment of the invention, it is preferred that the strengthening active substance is selected from at least one strengthening polymer from the group comprising strengthening non-ionic polymers, strengthening anionic polymers, strengthening amphoteric polymers, and strengthening cationic polymers.

Preferred aerosol compositions according to the invention include at least one strengthening cationic polymer. The strengthening cationic polymers have at least one structural unit that includes at least one permanently cationized nitrogen atom. Permanently cationized nitrogen atoms should be understood to include nitrogen atoms that bear a positive charge and thereby form a quaternary ammonium compound. Quaternary ammonium compounds are formed mostly by reacting tertiary amines with alkylating agents, such as methyl chloride, benzyl chloride, dimethyl sulfate, dodecyl bromide, and ethylene oxide. In particular, the following groups are known, in accordance with the tertiary amine used: alkylammonium compounds, alkenylammonium compounds, imidazolinium compounds, and pyridinium compounds.

Preferred aerosol compositions include the strengthening cationic polymer in an amount of 0.05 wt. % to 10 wt. %, especially preferably 0.075 wt. % to 8.0 wt. %, very especially preferably 0.1 wt. % to 5.0 wt. %, in each case with respect to the weight of said preparation.

According to the invention, the cationic strengthening polymers can be selected from cationic, quaternized cellulose derivatives. Cationic, quaternized celluloses that bear more than one permanent cationic charge in a side chain have proven to be advantageous. Cationic cellulose derivatives that are produced by reacting hydroxyethyl cellulose with a dimethyldiallylammonium reactant (particularly dimethyldiallylammonium chloride) optionally in the presence of further reactants are especially preferred. Among these cationic celluloses, in turn, the cationic celluloses having the INCI name Polyquaternium-4, which are sold for example under the names Celquat® H 100 and Celquat® L 200 by National Starch, are especially suitable. Preferred aerosol compositions are characterized in that the preparation a) includes at least one cationic cellulose derivative as a strengthening active substance.

Furthermore, cationic strengthening polymers that comprise at least one structural unit of formula (M-I) and at least one structural unit of formula (M-II) and optionally at least one structural unit of formula (M-III),

(M-I)

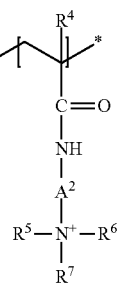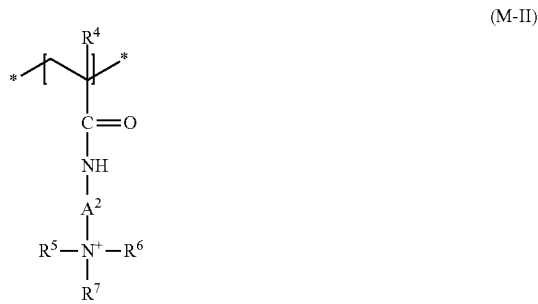
(M-II)

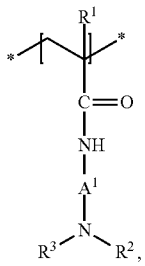

(M-III)

wherein

R¹ and R⁴ represent, independently of each other, a hydrogen atom or a methyl group, A¹ and A² represent, independently of each other, a group ethane-1,2-diyl, propane-1,3-diyl, or butane-1,4-diyl, R², R³, R⁵, and R⁶ represent, independently of each other, a ($C_1$ to $C_4$) alkyl group, R⁷ represents a ($C_8$ to $C_{30}$) alkyl group, are suitable.

All physiologically acceptable anions, such as chloride, bromide, hydrogen sulfate, methyl sulfate, ethyl sulfate, tetrafluoroborate, phosphate, hydrogen phosphate, dihydrogen phosphate, p-toluenesulfonate, or triflate, can be used to compensate the positive charge of this cationic polymer as of all further cationic polymers.

Suitable cationic polymers are commercially available, for example, as copolymers of dimethylaminoethyl methacrylate quaternized with diethyl sulfate, with N-vinylpyrrolidone, having the INCI name Polyquaternium-11, under the names Gafquat® 440, Gafquat® 734, Gafquat® 755 (each from ISP), and Luviquat PQ 11 PN (from BASF SE), copolymers of methacryloylaminopropyl lauryldimonium chloride with N-vinylpyrrolidone and dimethylaminopropyl methacrylamide, having the INCI name Polyquaternium-55, under the trade names Styleze® W-10, Styleze® W-20 (from ISP), copolymers of methacryloylaminopropyl lauryldimonium chloride with N-vinylpyrrolidone, N-vinylcaprolactam, and dimethylaminopropyl methacrylamide, having the INCI name Polyquaternium-69, under the trade name Aquastyle® 300 (from ISP).

Additional preferred cationic strengthening copolymers include at least one structural element of formula (M-IV),

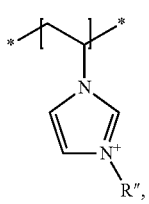

(M-IV)

wherein

R" represents a ($C_1$ to $C_4$) alkyl group, particularly a methyl group, and additionally at least one further cationic and/or non-ionic structural element.

In turn, in this embodiment it is preferred according to the invention if the preparation according to the invention includes, as a cationic strengthening polymer, at least one cationic copolymer that comprises, in addition to at least one structural element of formula (M-IV), a structural element of formula (M-I)

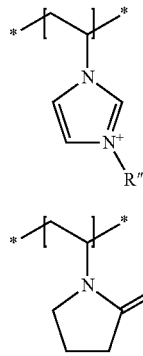

(M-IV)

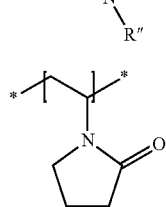

(M-I)

wherein

R" represents a ($C_1$ to $C_4$) alkyl group, particularly a methyl group. Very especially preferred cationic strengthening polymers include 10 to 30 mol %, preferably 15 to 25 mol %, and particularly 20 mol %, of structural units according to formula (M-IV) and 70 to 90 mol %, preferably 75 to 85 mol %, and particularly 80 mol %, of structural units of formula (M-I).

It is especially preferred if the cationic polymers include, in addition to polymer units that result from the incorporation of said structural units of formulas (M-IV) and (M-I) into the copolymer, at most 5 wt. %, preferably at most 1 wt. %, of polymer units that trace back to the incorporation of other monomers. Preferably, the copolymers (c1) are constructed exclusively of structural units of formula (M-IV) with R"=methyl and (M-I) and can be described by the general formula (Poly1),

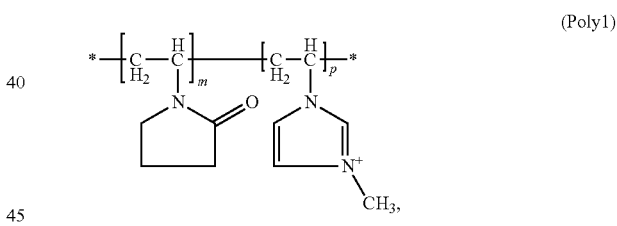

(Poly1)

wherein the indices m and p each vary in accordance with the molar mass of the polymer and should not mean that these copolymers are block copolymers. Rather, structural units of formula (M-IV) and of formula (M-I) can be statistically distributed in the molecule.

If a chloride ion is used to compensate the positive charge of the polymer of formula (Poly1), these N-methylvinylimidazole/vinylpyrrolidone copolymers are referred to as Polyquaternium-16 in accordance with INCI nomenclature and are available, for example, from BASF under the trade names Luviquat® Style, Luviquat® FC 370, Luviquat® FC 550, Luviquat® FC 905, and Luviquat® HM 552.

If a methosulfate is used to compensate the positive charge of the polymer of formula (Poly1), these N-methylvinylimidazole/vinylpyrrolidone copolymers are referred to as Polyquaternium-44 in accordance with INCI nomenclature and are available, for example, from BASF under the trade name Luviquat® UltraCare.

In addition to or instead of the one or more copolymers (c1), the agents according to the invention can also include copolymers (c2), which, proceeding from copolymer (c1), comprise structural units of formula (M-V),

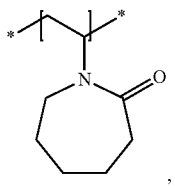
(M-V)

as additional structural units.

Additional especially preferred preparations according to the invention in this embodiment are therefore characterized in that they include, as a cationic strengthening polymer, at least one copolymer (c2) that includes at least one structural unit of formula (M-IV-a) and at least one structural unit of formula (M-I) and at least one structural unit of formula (M-V),

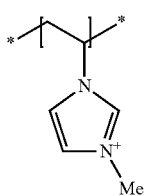
(M-IV-a)

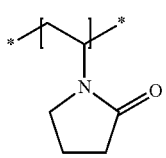
(M-I)

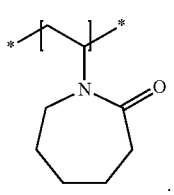
(M-V)

In this case as well, it is especially preferred in this embodiment if the copolymers (c2) include, in addition to polymer units that result from the incorporation of said structural units of formulas (M-IV-a), (M-I), and (M-V) into the copolymer, at most 5 wt. %, preferably at most 1 wt. %, of polymer units that trace back to the incorporation of other monomers. Preferably, the copolymers (c2) are constructed exclusively of structural units of formulas (M-IV-a), (M-I), and (M-V) and can be described by the general formula (Poly2),

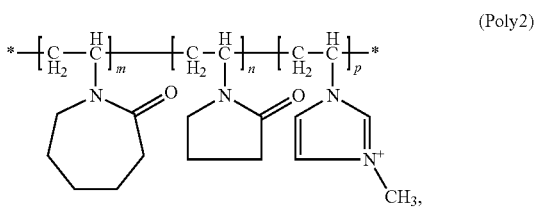
(Poly2)

wherein the indices m, n and p each vary in accordance with the molar mass of the polymer and should not mean that these copolymers are block copolymers. Rather, structural units of said formulas can be statistically distributed in the molecule.

If a methosulfate is used to compensate the positive charge of the polymer of formula (Poly2), such N-methyl-vinylimidazole/vinylpyrrolidone/vinylcaprolactam copolymers are referred to as Polyquaternium-46 in accordance with INCI nomenclature and are available, for example, from BASF under the trade name Luviquat® Hold.

Very especially preferred copolymers (c2) include 1 to 20 mol %, preferably 5 to 15 mol %, and particularly 10 mol %, of structural units of formula (M-IV-a), 30 to 50 mol %, preferably 35 to 45 mol %, and particularly 40 mol %, of structural units of formula (M-I), and 40 to 60 mol %, preferably 45 to 55 mol %, and particularly 60 mol %, of structural units of formula (M-V).

In addition to or instead of the one or more copolymers (c1) and/or (c2), the agents according to the invention can also include copolymers (c3) as a film-forming cationic and/or strengthening cationic polymer, which copolymers (c3) comprise, as structural units, structural units of formulas (M-IV-a) and (M-I), and further structural units from the group of the vinylimidazole units and further structural units from the group of the acrylamide and/or methacrylamide units.

Additional especially preferred preparations according to the invention in this embodiment are characterized in that they include, as a cationic strengthening polymer, at least one copolymer (c3) that includes at least one structural unit of formula (M-IV-a), at least one further structural unit of formula (M-I), at least one further structural unit of formula (M-VI), and at least one further structural unit according to formula (M-VII),

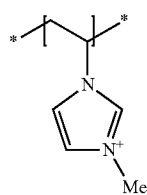
(M-VI-a)

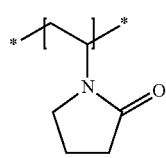
(M-I)

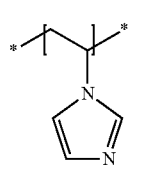
(M-VI)

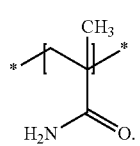
(M-VII)

In this case as well, it is especially preferred in this embodiment if the copolymers (c3) include, in addition to polymer units that result from the incorporation of said structural units of formulas (M-IV-a), (M-I), (M-VI), and (M-VII) into the copolymer, at most 5 wt. %, preferably at most 1 wt. %, of polymer units that trace back to the incorporation of other monomers. Preferably, the copolymers (c3) are constructed exclusively of structural units of formulas (M-IV-a), (M-I), (M-VI), and (M-VII) and can be described by the general formula (Poly3),

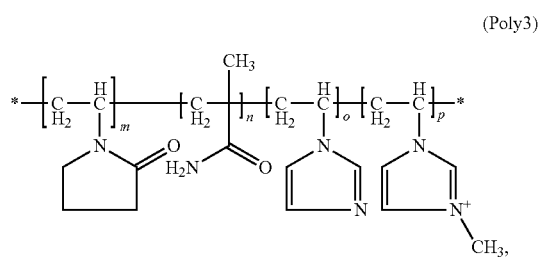

(Poly3)

wherein the indices m, n, o, and p each vary in accordance with the molar mass of the polymer and should not mean that these copolymers are block copolymers. Rather, structural units of formulas (M-IVa), (M-I), (M-VI), and (M-VII) can be statistically distributed in the molecule.

If a methosulfate is used to compensate the positive charge of the polymer of formula (Poly3), such N-methylvinylimidazole/vinylpyrrolidone/vinylimidazole/methacrylamide copolymers are referred to as Polyquaternium-68 in accordance with INCI nomenclature and are available, for example, from BASF under the trade name Luviquat® Supreme.

Very especially preferred copolymers (c3) include 1 to 12 mol %, preferably 3 to 9 mol %, and particularly 6 mol %, of structural units of formula (M-IV-a), 45 to 65 mol %, preferably 50 to 60 mol %, and particularly 55 mol %, of structural units of formula (M-I), 1 to 20 mol %, preferably 5 to 15 mol %, and particularly 10 mol %, of structural units of formula (M-VI), and 20 to 40 mol %, preferably 25 to 35 mol %, and particularly 29 mol %, of structural units of formula (M-VII).

Among the additional strengthening polymers selected from the cationic polymers having at least one structural element of formula (M-IV) above, the following are preferred:

N-vinylpyrrolidone/1-vinyl-3-methyl-1H-imidazolium chloride copolymers (such as polymers having the INCI name Polyquaternium-16, under the trade names Luviquat® Style, Luviquat® FC 370, Luviquat® FC 550, Luviquat® FC 905, and Luviquat® HM 552 (BASF SE)), N-vinylpyrrolidone/1-vinyl-3-methyl-1H-imidazolium methyl sulfate copolymers (such as polymers having the INCI name Polyquaternium-44, under the trade name Luviquat® Care (BASF SE)), N-vinylpyrrolidone/N-vinylcaprolactam/1-vinyl-3-methyl-1H-imidazolium terpolymer (such as polymers having the INCI name Polyquaternium-46, under the trade names Luviquat® Care or Luviquat® Hold (BASF SE)), N-vinylpyrrolidone/methacrylamide/N-vinylimidazole/1-vinyl-3-methyl-1H-imidazolium methyl sulfate copolymer (such as that having the INCI name Polyquaternium-68, under the trade name Luviquat® Supreme (BASF SE)), and mixtures of said polymers.

Preferred compositions according to the invention include at least one strengthening non-ionic polymer. Said strengthening non-ionic polymer can be included in the compositions as a sole polymer. However, it is especially preferred that the at least one strengthening non-ionic polymer is used in combination with at least one strengthening cationic polymer. In an especially preferred embodiment, the preparations b) include at least one strengthening non-ionic polymer and at least one strengthening cationic polymer.

According to the invention, a non-ionic polymer is understood to be a polymer that bears, in a protic solvent under standard conditions, substantially no structural units having permanently cationic or anionic groups, which can be compensated by counterions so as to maintain electroneutrality. Quaternized ammonium groups, for example, fall under cationic groups, but protonated amines do not. Carboxyl groups and sulfonic acid groups, for example, fall under anionic groups.

The strengthening non-ionic polymers are included in the preparation according to the invention in this embodiment preferably in an amount of 0.1 wt. % to 12.0 wt. %, especially preferably 0.2 wt. % to 10.0 wt. %, very especially preferably 0.5 wt. % to 8.0 wt. %, in each case with respect to the weight of said preparation.

According to the invention, strengthening non-ionic polymers that have at least one structural element of formula (M-VIII),

(M-VIII)

and that bear a hydrogen atom, an acetyl group, or a propanoyl group, particularly an acetyl group, as R' in accordance with formula (M-VIII) are preferably suitable.

In turn, the strengthening non-ionic polymers are preferably selected from at least one polymer of the group formed by homopolymers and non-ionic copolymers of N-vinylpyrrolidone, non-ionic copolymers of isobutene.

Suitable polyvinylpyrrolidones are, for example, commercial products such as Luviskol® K 90 or Luviskol® K 85 from BASF SE. Suitable polyvinylalcohols are sold, for example, by Du Pont under the trade name Elvanol® and by Air Products under the trade name Vinol® 523/540. Suitable polyvinyl acetate is sold, for example, by Air Products as an emulsion under the trade name Vinac®.

Agents that comprise at least one polymer selected from the group formed by polyvinylpyrrolidone, copolymers of N-vinylpyrrolidone and vinyl esters of carboxylic acids having 2 to 18 carbon atoms, particularly of N-vinylpyrrolidone and vinyl acetate, copolymers of N-vinylpyrrolidone and N-vinylimidazole and methacrylamide, copolymers of N-vinylpyrrolidone and N-vinylimidazole and acrylamide, copolymers of N-vinylpyrrolidone with N,N-di-($C_1$ to $C_4$)-alkylamino-($C_2$ to $C_4$)-alkylacrylamide, copolymers of N-vinylpyrrolidone with N,N-di-($C_1$ to $C_4$)-alkylamino-($C_2$ to $C_4$)-alkylacrylamide, as a strengthening non-ionic polymer are very especially preferred according to the invention.

Further possible preparations according to the invention in this embodiment having an additional non-ionic strengthening polymer are characterized in that they include, as a non-ionic strengthening polymer, at least one copolymer that includes at least one further structural unit of formula (M-I), at least one further structural unit of formula (M-VI), and at least one further structural unit of formula (M-VII),

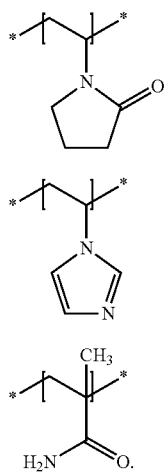

(M-I)

(M-VI)

(M-VII)

In this case as well, it is especially preferred if these copolymers include, in addition to polymer units that result from the incorporation of said structural units according to formulas (M-IV-a), (M-I), (M-VI), and (M-VII) into the copolymer, at most 5 wt. %, preferably at most 1 wt. %, of polymer units that trace back to the incorporation of other monomers. Preferably, the copolymers (c4) are constructed exclusively of structural units of formulas (M-IV-a), (M-I), (M-VI), and (M-VII) and can be described by the general formula (Poly4),

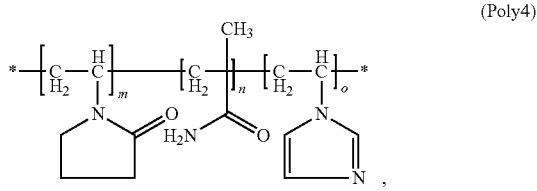

(Poly4)

wherein the indices m, n, o, and p each vary in accordance with the molar mass of the polymer and should not mean that these copolymers are block copolymers. Rather, structural units of formulas (M-I), (M-VI), and (M-VII) can be statistically distributed in the molecule.

An especially preferred polymer is selected from the polymers having the INCI name VP/Methacrylamide/Vinyl Imidazole Copolymer, which are available, for example, from BASF SE under the trade name Luviset Clear.

As follows from the statements above regarding the cationic strengthening polymers and the non-ionic strengthening polymers, aerosol compositions in the case of which the preparation b) includes at least one vinylpyrrolidone copolymer as a strengthening active substance (i) are especially preferred according to the invention.

Furthermore, aerosol compositions in which the preparation b) includes at least one non-ionic strengthening polymer and at least one cationic strengthening polymer as a strengthening active substance (i) are preferred.

Very especially preferred aerosol compositions are characterized in that the preparation b) includes at least one non-ionic strengthening polymer from the group of the vinylpyrrolidone copolymers and at least one cationic strengthening polymer from the group of the vinylpyrrolidone copolymers as a strengthening active substance (i).

The preparations according to the invention can also include at least one strengthening amphoteric polymer as a strengthening polymer. Polymers that include both free amino groups and free —COOH or $SO_3H$ groups in the molecule and are capable of forming inner salts, zwitterionic polymers that include quaternary ammonium groups and —COO$^-$ or —$SO_3^-$ groups in the molecule, and polymers that include —COOH or $SO_3H$ groups and quaternary ammonium groups are grouped under the term amphoteric polymers.

An example of a strengthening amphoteric polymer that can be used according to the invention is the acrylic resin available under the name Amphomer®, which is a copolymer of tert-butylaminoethyl methacrylate, N-(1,1,3,3-tetramethylbutyl)acrylamide, and two or more monomers from the group of acrylic acid, methacrylic acid, and the ($C_1$ to $C_4$) alkyl esters thereof. The latter have, in addition to the cationogenic group or positively charged group, at least one negatively charged group in the molecule and are also referred to as zwitterionic polymers.

The strengthening amphoteric polymers are included in the preparations according to the invention preferably in amounts of 0.1 wt. % to 20 wt. %, especially preferably 0.05 to 10 wt. %, in each case with respect to the weight of said preparation. Amounts of 0.1 to 5 wt. % are very especially preferred.

Furthermore, at least one film-forming anionic polymer can be used as a strengthening polymer.

Anionic polymers are anionic polymers that have carboxylate and/or sulfonate groups. Examples of anionic monomers of which such polymers can consist are acrylic acid, methacrylic acid, crotonic acid, maleic anhydride, and 2-acrylamido-2-methylpropane sulfonic acid. The acidic groups can be present completely or partially as a sodium, potassium, ammonium, or mono- or triethanol ammonium salt.

In this embodiment, it can be preferred that copolymers of at least one anionic monomer and at least one non-ionogenic monomer are used. With regard to the anionic monomers, reference is made to the substances stated above. Preferred non-ionogenic monomers are acrylamide, methacrylamide, acrylic acid esters, methacrylic acid esters, vinylpyrrolidone, vinyl ethers, and vinyl esters.

Preferred strengthening anionic polymers are acrylic acid/acrylamide copolymers and in particularly polyacrylamide copolymers having sulfonic-acid-group-containing monomers. An especially preferred strengthening anionic copolymer consists of 70 to 55 mol % of acrylamide and 30 to 45 mol % of 2-acrylamido-2-methylpropane sulfonic acid, wherein the sulfonic acid group is present completely or partially as a sodium, potassium, ammonium, or mono- or triethanol ammonium salt. This copolymer can also be present in a cross-linked state, wherein preferably polyolefinically unsaturated compounds such as tetraallyloxyethane, allyl sucrose, allyl pentaerythritol, and methylenebisacrylamide are used as cross-linking agents. Such a polymer is included in the commercial product Sepigel® 305 from SEPPIC. The use of this commercial product, which includes a hydrocarbon mixture ($C_{13}$-$C_{14}$ isoparaffin)

and a non-ionogenic emulsifier (Laureth-7) in addition to the polymer component, has proven to be especially advantageous in the teaching according to the invention.

The sodium acryloyldimethyl taurate copolymers sold as a compound with isohexadecane and polysorbate 80 under the name Simulgel® 600 have proven to be especially effective according to the invention.

Uncross-linked and cross-linked polyacrylic acids are likewise preferred strengthening anionic homopolymers. Allyl ethers of pentaerythritol, of sucrose, and of propylene can be preferred cross-linking agents. Such compounds are commercially available, for example, under the trademark Carbopol®.

Additional preferably usable strengthening anionic polymers are selected from at least one polymer of the group comprising copolymers of vinyl acetate and crotonic acid (which are marketed, for example, by CIBA in a 60 wt. % dispersion in isopropanol/water as the commercial product Aristoflex® A 60 having the INCI name VA/Crotonates Copolymer), copolymers of ethyl acrylate and methacrylic acid (which are sold, for example, by BASF SE in an approximately 20 to 30 wt. % dispersion in water and with an acid number of 84 to 105 under the trade name Luviflex® Soft, under the INCI name Acrylates Copolymer), polyurethanes having at least one carboxyl group (such as a copolymer of isophthalic acid, adipic acid, 1,6-hexanediol, neopentyl glycol, and isophorone diisocyanate, which are sold, for example, by BASF SE under the trade name Luviset PUR having the INCI name Polyurethane-1 or under the trade name Luviset Shape having the INCI name Polyurethane-34).

Alternatively or in combination with the strengthening polymers, preferred preparations b) include at least one wax as a strengthening active substance. Aerosol compositions comprising a preparation b) that includes at least one wax as a strengthening active substance are preferred according to the invention. Waxes used in the context of the invention are kneadable at 20° C., solid to brittle and hard, coarse to finely crystalline, translucent to opaque, but not glassy, and melt above 40° C. without decomposition. Waxes differ from similar synthetic or natural products (e.g., resins, plastic masses, metallic soaps, etc.) in that they go into the molten, low-viscosity state from 40° C. to 90° C.

Waxes that have a melting point in the range of 50° C. to 85° C., particularly 60° C. to 75° C., at 1013 mbar are preferred according to the invention.

The waxes are preferably selected from plant, animal, and mineral waxes. Waxes that can be used according to the invention are natural waxes (plant waxes: cotton wax, carnauba wax, candelilla wax, esparto wax, guaruma wax, Japan wax, cork wax, montan wax, ouricury wax, rice germ oil wax, sugarcane wax; animal waxes: beeswax, preen oil, wool wax, shellac wax (see shellac), spermaceti; mineral waxes: micro waxes, ceresin, ozokerite), chemically modified waxes (hard waxes: hydrogenated jojoba waxes (see jojoba oil), montan wax, Sasol waxes), and synthetic waxes (polyalkylene waxes (such as polyolefin waxes, polyethylene waxes, polypropylene waxes), polyethylene glycol waxes, amide waxes). Beeswax (cera alba), carnauba wax, candelilla wax, montan wax, microcrystalline waxes (microcrystalline paraffins), and cetyl palmitate are especially preferred according to the invention.

The teaching according to the invention also comprises the combined use of several waxes in the preparations according to the invention. Thus, small amounts of carnauba wax, for example, can be added to increase the melting point and dropping point of another wax. Furthermore, a series of wax mixtures, optionally mixed with further additives, is commercially available. The wax mixtures available under the names "Spezialwachs 7686 OE" (a mixture of cetyl palmitate, beeswax, microcrystalline wax, and polyethylene having a melting range of 73-75° C.; manufacturer: Kahl & Co), Polywax® GP 200 (a mixture of stearyl alcohol and polyethylene glycol stearate having a melting point of 47-51° C.; manufacturer: Croda), and "Weichceresin® FL 400" (a petrolatum/paraffin oil/wax mixture having a melting point of 50-54° C.; manufacturer: Parafluid Mineralolgesellschaft) are examples of mixtures preferably used according to the invention.

The aerosol compositions according to the invention include the waxes preferably in amounts of 0.1 to 10 wt. % and particularly 0.2 to 5.0 wt. % with respect to the total weight of the aerosol compositions according to the invention.

In aerosol compositions preferred according to the invention, the percentage of the strengthening active substance by weight with respect to the total weight of the aerosol composition is 0.5 to 12 wt. %, preferably 1.0 to 10 wt. %, and particularly 2.0 to 8.0 wt. %.

A further essential constituent of the preparation b) is an alkoxylated carboxylic acid ester of the previously stated formula (I). The incorporation of at least one ester according to formula (I) into the aerosol compositions according to the invention has the result that they bring about a very good care effect on the hair treated with them without negatively affecting the hold of the hair.

In preferred esters according to formula (I), the group R1 represents a straight-chain, saturated alkyl group, which preferably has 8 to 18 carbon atoms. The group R1 especially preferably represents a decyl, lauryl, myristyl, palmityl, or stearyl group and particularly preferably represents a myristyl group.

In also preferred esters according to formula (I), the group R2 represents a methyl group or an ethyl group, preferably a methyl group, and the groups R3 and R4 represent identical groups, preferably —H or a methyl group and particularly preferably hydrogen.

In also preferred esters according to formula (I), the group R5 has the same meaning as the group R1 or the group R5 represents a phenyl group optionally substituted with one or more hydroxyl groups, amino groups, methyl groups, ethyl groups, methoxy groups, or ethoxy groups. The group R5 preferably represents an unsubstituted phenyl group.

The indices n and m represent, independently of each other, preferably the number 0 or a number from 1 to 10. Especially preferably, n represents a number from 1 to 10, preferably from 2 to 7, and particularly from 3 to 5, and m represents the number 1, 2, or 3, preferably 1 or 2, and particularly the number 1.

An especially suitable carboxylic acid ester according to formula (I) is characterized in that the group R1 represents a myristyl group, R2 represents a methyl group, the groups R3 and R4 represent hydrogen, R5 represents an unsubstituted phenyl group, n represents the number 3, and M represents the number 1.

Such esters are known under the INCI name PPG-3 Benzyl Ether Myristate and are commercially available from different providers, for example from Croda under the trade name Crodamol STS®.

In an especially preferred embodiment, aerosol compositions according to the invention are characterized in that the preparation b) includes an alkoxylated carboxylic acid ester according to formula (I), in which R1 represents a straight-chain, saturated alkyl group having 8 to 18 carbon atoms, preferably a decyl, lauryl, myristyl, palmityl, or stearyl group, R2 represents a methyl group, R3 and R4 both represent hydrogen, R5 represents a phenyl group, n represents a number from 1 to 10, preferably from 2 to 7, and m represents the number 1 or 2.

The percentage of the at least one carboxylic acid ester according to formula (I) by weight with respect to the total weight of the aerosol composition is preferably 0.1 to 5.0 wt. %, more preferably 0.2 to 3.0 wt. %, and particularly 0.3 to 2.0 wt. %.

The aerosol preparations according to the invention comprise at least one propellant a) as a further constituent in addition to the cosmetic preparation b). Preferred propellants a) include at least one propellant from the group of propane and butane. Especially preferred is a mixture of propane and butane in a weight ratio of propane to butane of 5:1 to 1:5, preferably 4:1 to 1:4, and particularly 3:1 to 1:3.

Especially preferred aerosol compositions are characterized in that the propellant a) is selected from propane and/or butane, wherein the joint percentage of propane and/or butane by weight with respect to the total weight of the aerosol composition is 1-99.5 wt. %, preferably 4 to 50 wt. %.

The aerosol composition according to the invention is preferably formulated in a pressure container. According to the invention, a "pressure container" is a container that has a higher gas pressure in the interior than outside the container and from which a gas flow can be withdrawn via a valve. Pressure containers by means of which a product (e.g., a liquid composition) is dispensed via a valve by means of the internal gas pressure of the container are referred to as "aerosol dispensing containers" by definition. It is especially preferred that the aerosol composition is formulated in an aerosol dispensing container.

Conversely to the aerosol definition, a container under standard pressure, by means of which a product can be dispensed by a pumping or squeezing system by means of mechanical action, is defined as a "non-aerosol dispensing container".

The aerosol compositions according to the invention can be produced in the typical manner. In general, all constituents of the preparation of the aerosol composition according to the invention are introduced into a suitable pressure-resistant container. The container is then closed with a valve. Finally, the desired amount of the specific propellant is introduced by means of conventional techniques.

Vessels composed of metal (aluminum, tinplate, tin), protected and/or non-splintering plastic, or glass coated with plastic on the outside are possible as pressure-resistant containers. Pressure resistance, fracture strength, corrosion resistance, ease of filling, aesthetic aspects, ease of handling, printability, etc. play a role in the selection of these vessels. Specific internal protective coatings ensure corrosion resistance with respect to the agent formulated in the pressure container. The valves used especially preferably have an internally coated valve plate, wherein the coating and the valve material are compatible with each other. If aluminum valves are used, their valve plates can be internally coated, for example, with Micoflex coating. If tinplate valves are used according to the invention, their valve plates can be internally coated, for example, with PET (polyethylene terephthalate).

The compositions according to the invention can also be packaged in a multi-chamber dispenser. The multi-chamber dispenser can also be used in such a way that one chamber is filled with the compressed propellant and another chamber is filled with the remaining constituents of the aerosol composition according to the invention. A bag-in-can package, for example, is such a multi-chamber dispenser.

The cosmetic preparations b) according to the invention include the ingredients and active substances in a cosmetically acceptable carrier.

Preferred cosmetically acceptable carriers are aqueous, alcoholic, or aqueous-alcoholic media having preferably at least 5 wt. % water with respect to the entire preparation. The water content of the cosmetic preparations b) according to the invention is preferably 5 to 97 wt. %. In the embodiment as an aerosol spray, it is preferably 5 to 30 wt. %. In the embodiment as an aerosol foam, it is preferably 30 to 95 wt. %.

In particular, the lower alcohols having 1 to 4 carbon atoms typically used for cosmetic purposes, such as ethanol and isopropanol, can be included as alcohols.

Preferred aerosol compositions are characterized in that the aerosol composition includes 50 to 98 wt. %, preferably 60 to 95 wt. %, and particularly 70 to 90 wt. %, of water and/or ethanol with respect to the total weight of the aerosol composition.

The flexibility of the hold formed when the aerosol composition according to the invention is applied can be increased by adding propylene glycol and/or polyethylene glycol and/or polypropylene glycol. Thus, if a more flexible hold is desired, the aerosol compositions according to the invention include preferably 0.01 to 30 wt. % of polyethylene glycol and/or polypropylene glycol with respect to the total weight of the aerosol compositions according to the invention.

The cosmetic preparations b) preferably have a pH value of 2 to 11. The pH range between 2 and 8 is especially preferred. In this document, the specifications regarding the pH value relate to the pH value at 25° C., unless otherwise noted.

The effects according to the invention can be increased by adding at least one ($C_2$ to $C_6$) trialkyl citrate to the preparation b) according to the invention. Therefore, it is preferred according to the invention if the preparation b) additionally includes at least one compound of formula (E), $$R^1OOC\diagdown\diagup COOR^2 \atop HO\diagup\diagdown COOR^3 \qquad (E)$$

wherein
$R^1$, $R^2$, and $R^3$ represent, independently of each other, a ($C_2$ to $C_6$) alkyl group.

Examples of a ($C_2$ to $C_6$) alkyl group according to formula (E) are methyl, ethyl, isopropyl, n-propyl, n-butyl, sec-butyl, isobutyl, tert-butyl, n-pentyl, neopentyl, isopentyl, and n-hexyl. Triethyl citrate has proven to be an especially effective compound of formula (E). The cosmetic preparation b) according to the invention includes the compounds of formula (E) preferably in an amount of 0.01 to 1 wt. %, particularly 0.05 to 0.3 wt. %, in each case with respect to the weight of said preparation.

The preparations b) according to the invention preferably additionally include at least one surfactant, wherein in principle non-ionic, anionic, cationic, and ampholytic surfactants are suitable. The group of the ampholytic or amphoteric surfactants comprises zwitterionic surfactants and ampholytes. According to the invention, the surfactants can already have an emulsifying effect.

The use of at least one non-ionic surfactant and/or at least one cationic surfactant is preferred in this embodiment of the invention.

The additional surfactants are included in the preparation according to the invention preferably in an amount of 0.01 wt. % to 5 wt. %, especially preferably 0.05 wt. % to 0.5 wt. %, in each case with respect to the weight of said preparation.

It has proven to be especially preferred if the cosmetic preparations b) according to the invention additionally include at least one cationic surfactant.

It was possible to increase the care properties of the aerosol compositions according to the invention even further by adding the cationic surfactant to the preparation b), without the hold of the hairstyle being thereby impaired.

Especially suitable cationic surfactants are preferably selected from surfactants of the type of the quaternary ammonium compounds, the esterquats, and/or the amidoamines. Preferred quaternary ammonium compounds are ammonium halides, particularly chlorides and bromides, such as alkyltrimethylammonium chlorides, dialkyldimethylammonium chlorides, and trialkylmethylammonium chlorides. The long alkyl chains of these surfactants have preferably 10 to 18 carbon atoms, for example in cetyltrimethylammonium chloride, stearyltrimethylammonium chloride, distearyldimethylammonium chloride, lauryldimethylammonium chloride, lauryldimethylbenzylammonium chloride, and tricetylmethylammonium chloride. Additional preferred cationic surfactants are the imidazolium compounds known under the INCI names Quaternium-27 and Quaternium-83.

Especially preferred are alkyltrimethylammonium chlorides, dialkyldimethylammonium chlorides, and trialkylmethylammonium chlorides, in which the long alkyl chains have preferably 10 to 18 carbon atoms. Cetyltrimethylammonium chloride and/or stearyltrimethylammonium chloride is particularly preferred.

The one or more cationic surfactants are used in the aerosol compositions according to the invention preferably in a percentage by weight of 0.02 to 5.0 wt. %, preferably 0.05 to 3 wt. %, and particularly 0.1 to 2 wt. %, with respect to the total weight of the aerosol compositions.

Furthermore, it has proven to be especially preferred if the cosmetic preparations b) according to the invention additionally include at least one non-ionic surfactant.

Non-ionic surfactants include, for example, a polyol group, a polyalkylene glycol ether group, or a combination of polyol group and polyglycol ether group as a hydrophilic group. Such compounds are, for example, products of the addition of 2 to 100 mol of ethylene oxide and/or 1 to 5 mol of propylene oxide to linear and branched fatty alcohols having 8 to 30 carbon atoms, to fatty acids having 8 to 30 carbon atoms, and to alkylphenols having 8 to 15 carbon atoms in the alkyl group, products of the addition of 2 to 50 mol of ethylene oxide and/or 1 to 5 mol of propylene oxide to linear and branched fatty alcohols having 8 to 30 carbon atoms, to fatty acids having 8 to 30 carbon atoms, and to alkylphenols having 8 to 15 carbon atoms in the alkyl group, said products being end-capped with a methyl group or $C_2$-$C_6$ alkyl group, such as the products available under the names Dehydol® LS, Dehydol® LT (Cognis), $C_{12}$-$C_{30}$ fatty acid mono- and diesters of products of the addition of 1 to 30 mol of ethylene oxide to glycerol, products of the addition of 5 to 60 mol of ethylene oxide to castor oil and castor wax, polyol fatty acid esters, such as the commercial product Hydagen® HSP (Cognis) or Sovermol types (Cognis), alkoxylated triglycerides, alkoxylated fatty acid alkyl esters of formula (T-I),

$$R^1CO\text{---}(OCH_2CHR^2)_w OR^3 \qquad (T\text{-}I),$$

in which $R^1CO$ represents a linear or branched, saturated and/or unsaturated acyl group having 6 to 22 carbon atoms, $R^2$ represents hydrogen or methyl, $R^3$ represents linear or branched alkyl groups having 1 to 4 carbon atoms, and w represents numbers from 1 to 20, amine oxides, hydroxy mixed ethers, which are described, for example, in DE-OS 19738866, sorbitan fatty acid esters and products of the addition of ethylene oxide to sorbitan fatty acid esters such as the polysorbates, sugar fatty acid esters and products of the addition of ethylene oxide to sugar fatty acid esters, products of the addition of ethylene oxide to fatty acid alkanolamides and fatty amines, sugar surfactants of the type of the alkyl and alkenyl oligoglycosides according to formula (T-II),

$$R^4O\text{---}[G]_p \qquad (T\text{-}II),$$

in which $R^4$ represents an alkyl group or alkenyl group having 4 to 22 carbon atoms, G represents a sugar group having 5 or 6 carbon atoms, and p represents numbers from 1 to 10. They can be obtained in accordance with the pertinent methods of preparative organic chemistry.

The alkyl and alkenyl oligoglycosides can be derived from aldoses or ketoses having 5 or 6 carbon atoms, preferably from glucose. The preferred alkyl and/or alkenyl oligoglycosides are therefore alky and/or alkenyl oligoglucosides. The index number p in the general formula (T-II) indicates the degree of oligomerization (DP), i.e., the distribution of mono- and oligoglycosides, and represents a number between 1 and 10. While p should always be an integer in the individual molecular and can especially assume the values p=1 to 6 here, for a certain alkyl oligoglycoside the value p is an analytically determined calculated quantity, which is usually a fraction. Alkyl and/or alkenyl oligoglycosides having an average degree of oligomerization p of 1.1 to 3.0 are preferably used. From the perspective of application technology, alkyl and/or alkenyl oligoglycosides whose degree of oligomerization is less than 1.7 and lies in particular between 1.2 and 1.4 are preferred. The alkyl group or alkenyl group $R^4$ can be derived from primary alcohols having 4 to 11, preferably 8 to 10, carbon atoms. Typical examples are butanol, 1-hexanol, capryl alcohol, capric alcohol, and undecyl alcohol and their technical mixtures, which are obtained for example in the hydrogenation of technical fatty acid methyl esters or in the course of the hydrogenation of aldehydes form the Roelen oxo synthesis. Alkyl oligoglucosides of the chain length $C_8$-$C_{18}$ (DP=1 to 3), which arise as the forerun in the separation of technical $C_8$-$C_{18}$ coconut fatty alcohol by distillation and can be impurified with a fraction of less than 6 wt. % of $C_{12}$ alcohol, and alkyl oligoglucosides based on technical C$_{9/11}$ oxo alcohols (DP=1 to 3) are preferred. The alky group or alkenyl group R$^4$ can also be derived from primary alcohols having 12 to 22, preferably 12 to 14, carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachidyl alcohol, gadoleyl alcohol, behenyl alcohol, erucyl alcohol, brassidyl alcohol, and their technical mixtures, which can be obtained as described above. Alkyl oligoglucosides based on hardened C$_{12/14}$ coconut alcohol and having a DP of 1 to 3 are preferred.

The alkylene oxide addition products of the addition of 2 to 100 mol of ethylene oxide per mole of fatty alcohol or fatty acid to saturated linear fatty alcohols and fatty acids have proven to be very especially preferred non-ionic surfactants. Preparations having excellent properties are likewise obtained if they include C$_{12}$-C$_{30}$ fatty acid mono- and diesters of products of the addition of 1 to 30 mol of ethylene oxide to glycerol and/or products of the addition of 5 to 60 mol of ethylene oxide to castor oil and castor wax as non-ionic surfactants.

The preparations according to the invention very especially preferably include as a surfactant at least one product of the addition of 15 to 100 mol of ethylene oxide, particularly 15 to 50 mol of ethylene oxide, to a linear or branched (particularly linear) fatty alcohol having 8 to 22 carbon atoms and/or to castor oil, said product very especially preferably being Ceteareth-15, Ceteareth-25, or Ceteareth-50, which are marketed as Eumulgin® CS 15 (COGNIS), Cremophor A25 (BASF SE), and Eumulgin® CS 50 (COGNIS), respectively, or being PEG-40 Hydrogenated Castor Oil, which is marketed as Eumulgin® CO 455.

Preferred aerosol compositions are characterized in that the preparation b) includes at least one non-ionic surfactant, preferably a non-ionic surfactant from the group of the alkoxylated fatty alcohols and/or of alkoxylated castor oil.

In principle, all anionic surface-active substances suitable for use on the human body are suitable as anionic surfactants. They are characterized by a water-solubilizing anionic group, such as a carboxylate, sulfate, sulfonate, or phosphate group, and a lipophilic alkyl group having approximately 8 to 30 carbon atoms. In addition, glycol or polyglycol ether groups, ester groups, ether groups, amide groups, and hydroxyl groups can be included in the molecule. Examples of suitable anionic surfactants are, in each case in the form of the sodium, potassium, ammonium, and mono-, di-, and trialkanolammonium salts having 2 to 4 carbon atoms in the alkanol group, linear and branched fatty acids having 8 to 30 carbon atoms (soaps),
ether carboxylic acids of the formula R—O—(CH$_2$—CH$_2$O)$_x$—CH$_2$—COOH, in which R is a linear alkyl group having 8 to 30 carbon atoms and x=0 or 1 to 16,
acyl sarcosides having 8 to 24 carbon atoms in the acyl group,
acyl taurides having 8 to 24 carbon atoms in the acyl group,
acyl isethionates having 8 to 24 carbon atoms in the acyl group,
sulfosuccinic acid mono- and dialkyl esters having 8 to 24 carbon atoms in the alkyl group and sulfosuccinic acid monoalkyl polyoxyethyl esters having 8 to 24 carbon atoms in the alkyl group and 1 to 6 oxyethyl groups,
linear alkane sulfonates having 8 to 24 carbon atoms,
linear alpha-olefin sulfonates having 8 to 24 carbon atoms,
alpha-sulfo fatty acid methyl esters of fatty acids having 8 to 30 carbon atoms,
alkyl sulfates and alkyl polyglycol ether sulfates of the formula R—O (CH$_2$—CH$_2$O)$_x$—OSO$_3$H, in which R is a preferably linear alkyl group having 8 to 30 carbon atoms and x=0 or 1 to 12,
mixtures of surface-active hydroxysulfonates,
sulfated hydroxyalkyl polyethylene glycol ethers and/or hydroxyalkylene propylene glycol ethers,
sulfonates of unsaturated fatty acids having 8 to 24 carbon atoms and 1 to 6 double bonds,
esters of tartaric acid and citric acid with alcohols that are products of the addition of approximately 2 to 15 molecules of ethylene oxide and/or propylene oxide to fatty alcohols having 8 to 22 carbon atoms,
alkyl and/or alkenyl ether phosphates of formula (T-V),

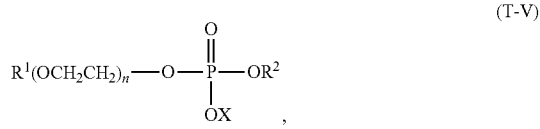

(T-V)

in which R$^1$ preferably represents an aliphatic hydrocarbon group having 8 to 30 carbon atoms, R$^2$ represents hydrogen, a group (CH$_2$CH$_2$O)$_n$R$^1$, or X, n represents numbers from 1 to 10, and X represents hydrogen, an alkali metal or alkaline-earth metal, or NR$^3$R$^4$R$^5$R$^6$, with R$^3$ to R$^6$ representing, independently of each other, hydrogen or a C$_1$ to C$_4$ hydrocarbon group,
sulfated fatty acid alkylene glycol esters of formula (T-VI),

R$^7$CO(AlkO)$_n$SO$_3$M          (T-VI), in which R$^7$CO— represents a linear or branched, aliphatic, saturated and/or unsaturated acyl group having 6 to 22 carbon atoms, Alk represents CH$_2$CH$_2$, CHCH$_3$CH$_2$, and/or CH$_2$CHCH$_3$, n represents numbers from 0.5 to 5, and M represents a cation,
monoglyceride sulfates and monoglyceride ether sulfates of the formula (T-VII),

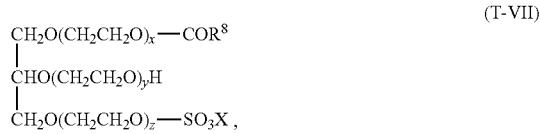

(T-VII)

in which R$^8$CO, represents a linear or branched acyl group having 6 to 22 carbon atoms, x, y, and z represent 0 or numbers from 1 to 30, preferably 2 to 10, in total, and X represents an alkali metal or alkaline-earth metal. Typical examples of monoglyceride (ether) sulfates suitable according to the invention are the products of the reaction of lauric acid monoglyceride, coconut fatty acid monoglyceride, palmitic acid monoglyceride, stearic acid monoglyceride, oleic acid monoglyceride, and tallow fatty acid monoglyceride and their ethylene oxide adducts with sulfur trioxide or chlorosulfuric acid, in the form of their sodium salts. Monoglyceride sulfates of formula (T-VII), in which R$^8$CO represents a linear acyl group having 8 to 18 carbon atoms, are preferably used,
amide ether carboxylic acids,
products of the condensation of C$_8$-C$_{30}$ fatty alcohols with protein hydrolysates and/or amino acids and derivatives thereof, which are known to a person skilled in the art as protein fatty acid condensates, such as the Lamepon® types, the Gluadin® types, Hostapon® KCG, or the Amisoft® types.

The term "zwitterionic surfactants" refers to surface-active compounds that bear at least one quaternary ammonium group and at least one —COO$^{(-)}$ or —SO$_3^{(-)}$ group in the molecule. Especially suitable zwitterionic surfactants are the betaines, such as the N-alkyl-N,N-dimethylammonium glycinates, for example coco alkyl dimethylammonium glycinate, N-acyl-aminopropyl-N,N-dimethylammonium glycinates, for example coco acyl aminopropyl dimethylammonium glycinate, 2-alkyl-3-carboxymethyl-3-hydroxyethylimidazolines having 8 to 18 C atoms in the alkyl or acyl group in each case, and coco acyl aminoethyl hydroxyethyl carboxymethyl glycinate. A preferred zwitterionic surfactant is the fatty acid amide derivative known under the INCI name Cocamidopropyl Betaine.

Ampholytes are understood to include surface-active compounds that include at least one free amino group and at least one —COOH or —SO$_3$H group in addition to a $C_8$-$C_{24}$ alkyl group or acyl group in the molecule and are capable of forming inner salts. Examples of suitable ampholytes are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsacrosines, 2-alkylaminopropionic acids, and alkylaminoacetic acids having approximately 8 to 24 carbon atoms in the alkyl group in each case. Especially preferred ampholytes are N-cocoalkylaminopropionate, cocoacylaminoethyl-aminopropionate, and $C_{12}$-$C_{18}$ acylsarcosine.

In an embodiment preferred according to the invention, the cosmetic preparations b) additionally include at least one silicone oil. The silicone oils include, e.g., dialkyl- and alkylarylsiloxanes, such as cyclopentasiloxane, cyclohexasiloxane, dimethylpolysiloxane, and methylphenylpolysiloxane, and also hexamethyldisiloxane, octamethyltrisiloxane, and decamethyltetrasiloxane. Especially preferred are volatile linear silicone oils, particularly hexamethyldisiloxane ($L_2$), octamethyltrisiloxane ($L_3$), decamethyltetrasiloxane ($L_4$), dodecamethylpentasiloxane ($L_5$), and any two-, three-, and four-component mixtures of $L_2$, $L_3$, $L_4$, and/or $L_5$, which are included, for example, in the commercial products Dow Corning 2-1184 Fluid, Dow Corning® 200 (0.65 cSt), and Dow Corning® 200 (1.5 cSt) from Dow Corning, wherein the values of the kinematic viscosity relate to a temperature of 25° C.

In addition to the aforementioned substances typically referred to as "volatile" silicone oils and in addition to the aforementioned volatile non-silicone oils, cosmetic preparations a) especially preferred according to the invention can also include at least one non-volatile cosmetic oil selected from non-volatile silicone oils and non-volatile non-silicone oils.

Preferred non-volatile silicone oils are selected from high-molecular-weight linear dimethylpolysiloxanes commercially available, for example, under the name Dow Corning® 190, Dow Corning® 200 Fluid having kinematic viscosities (25° C.) in the range of 5 to 100 cSt, preferably 5 to 50 cSt or even 5 to 10 cSt, and Baysilon® 350 M (having a kinematic viscosity (25° C.) of approximately 350 cSt).

The present invention also relates to the use of an aerosol composition according to the invention to temporarily shape keratin fibers.

EXAMPLES

The composition of some preferred cosmetic aerosol compositions can be found in the following tables (the specifications each relate to wt. % AS of the particular component with respect to the total weight of the aerosol composition, unless otherwise indicated).

TABLE 1

|  | A | B | C | D | E |
|---|---|---|---|---|---|
| Butane | 1.0-40.0 | 1.0-40.0 | 1.0-40.0 | 1.0-40.0 | 1.0-40.0 |
| Propane | 1.0-40.0 | 1.0-40.0 | 1.0-40.0 | 1.0-40.0 | 1.0-40.0 |
| VP/VA Copolymer (Luviskol VA 64 ® Powder) | 2.0-4.0 | 2.0-4.0 | 2.0-4.0 |  |  |
| VP/Methacrylamide/Vinyl Imidazole Copolymer (Luviset Clear ®) |  |  |  | 2.0-4.0 | 2.0-4.0 |
| PPG-3 Benzyl Ether Myristate (Crodamol STS-LQ ®) | 0.5-3.0 | 0.5-3.0 | 0.5-3.0 | 0.5-3.0 | 0.5-3.0 |
| Polyquaternium-11 (Gafquat 755 ®) | 0.1-3.0 |  |  | 0.1-3.0 |  |
| Polyquaternium-16 (Luviquat FC 550 ®) |  | 0.1-3.0 |  |  |  |
| Polyquaternium-44 (Luviquat Care ®) |  |  | 0.1-3.0 |  | 0.1-3.0 |
| Propylene glycol | 0.1-5.0 | 0.1-5.0 | 0.1-5.0 | 0.1-5.0 | 0.1-5.0 |
| Cetrimonium chloride | 0.1-2.0 | 0.1-2.0 |  | 0.1-2.0 |  |
| Steartrimonium chloride |  |  | 0.1-2.0 |  | 0.1-2.0 |
| PEG-40 Hydrogenated Castor Oil | 0.1-2.0 | 0.1-2.0 | 0.1-2.0 | 0.1-2.0 | 0.1-2.0 |
| Panthenol | 0.1-1.0 | 0.1-1.0 |  | 0.1-1.0 |  |
| Preservative (sodium benzoate, phenoxyethanol) | qs | qs | qs | qs | qs |
| Acids for setting pH (lactic acid, citric acid) | qs | qs | qs | qs | qs |
| Water | ad 100 | ad 100 | ad 100 | ad 100 | ad 100 |

TABLE 2

|  | A | B | C | D | E |
|---|---|---|---|---|---|
| Butane | 1.5-15.0 | 1.5-15.0 | 1.5-15.0 | 1.5-15.0 | 1.5-15.0 |
| Propane | 1.5-15.0 | 1.5-15.0 | 1.5-15.0 | 1.5-15.0 | 1.5-15.0 |
| VP/VA Copolymer (Luviskol VA 64 ® Powder) | 2.0-3.0 | 2.0-3.0 | 2.0-3.0 | | |
| VP/Methacrylamide/Vinyl Imidazole Copolymer (Luviset Clear ®) | | | | 2.0-3.0 | 2.0-3.0 |
| PPG-3 Benzyl Ether Myristate (Crodamol STS-LQ ®) | 0.5-1.5 | 0.5-2.0 | 0.5-1.5 | 0.5-1.5 | 0.5-2.0 |
| Polyquaternium-11 (Gafquat 755 ®) | 0.2-1.0 | | | 0.1-1.0 | |
| Polyquaternium-16 (Luviquat FC 550 ®) | | 0.2-1.0 | | | |
| Polyquaternium-44 (Luviquat Care ®) | | | 0.1-1.0 | | 0.1-1.0 |
| Propylene glycol | 0.5-2.0 | 0.5-3.0 | 0.5-2.0 | 0.5-3.0 | 0.5-3.0 |
| Cetrimonium chloride | 0.2-1.0 | 0.2-1.0 | | 0.2-1.0 | |
| Steartrimonium chloride | | | 0.2-1.0 | | 0.2-1.0 |
| PEG-40 Hydrogenated Castor Oil | 0.2-1.0 | 0.2-1.0 | 0.2-1.0 | 0.2-1.0 | 0.2-1.0 |
| Panthenol | 0.1-0.5 | 0.1-0.5 | | 0.1-0.5 | |
| Preservative (sodium benzoate, phenoxyethanol) | qs | qs | qs | qs | qs |
| Acids for setting pH (lactic acid, citric acid) | qs | qs | qs | qs | qs |
| Water | ad 100 | ad 100 | ad 100 | ad 100 | ad 100 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An aerosol composition, comprising
   a) at least one propellant and
   b) at least one cosmetic preparation, comprising
      (i) 0.075 wt % to 8.0 wt % of copolymers of methacryl methacryloylaminopropyl lauryldimonium chloride with N-vinylpyrrolidone and dimethylaminopropyl methacrylamide and N-methylvinylimidazole/vinylpyrrolidone copolymers
      (ii) 0.3 to 2.0 wt. % of at least one alkoxylated carboxylic acid ester of the following formula (1),

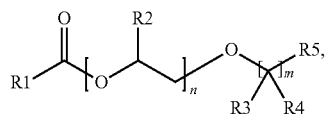
(I)

in which
R1 represents a straight-chain or branched, saturated or unsaturated alkyl group having 6 to 24 carbon atoms,
R2 represents hydrogen or an alkyl group having 1 to 4 carbon atoms,
R3 and R4 represent, independently of each other, hydrogen or an alkyl group having 1 to 4 carbon atoms,
R5 represents a straight-chain or branched, saturated or unsaturated alkyl group having 6 to 24 carbon atoms or a phenyl group, and
n and m represent, independently of each other, the numbers 0 or 1 to 20, and
c) 50 to 98 wt. % water and/or ethanol with respect to the total weight of the aerosol composition
d) 0.5 to 3 wt. %, based on the total weight of the composition, of at least one cationic surfactant being selected from the group consisting of alkyltrimethylammonium chlorides, dialkyldimethylammonium chlorides, and trialkylmethylammonium chlorides, and
e) at least one non-ionic surfactant.

2. The aerosol composition according to claim 1, wherein the preparation b) includes an alkoxylated carboxylic acid ester according to formula (1),

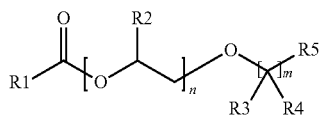

in which R1 represents a straight-chain, saturated alkyl group having 8 to 18 carbon atoms, preferably a decyl, lauryl, myristyl, palmityl, or stearyl group,
R2 represents a methyl group,
R3 and R4 both represent hydrogen,
R5 represents a phenyl group,
n represents a number from 1 to 10, and
m represents the number 1 or 2.

3. The aerosol composition according to claim 1, wherein the aerosol composition further comprises 70 to 90 wt. % water and/or ethanol with respect to the total weight of the aerosol composition.

4. The aerosol composition according to claim 1, wherein the propellant a) is selected from propane and/or butane, wherein the joint percentage of propane and/or butane by weight with respect to the total weight of the aerosol composition is 1-99.5 wt. %.

* * * * *